(12) United States Patent
Kokish et al.

(10) Patent No.: US 7,211,150 B1
(45) Date of Patent: May 1, 2007

(54) APPARATUS AND METHOD FOR COATING AND DRYING MULTIPLE STENTS

(75) Inventors: Arkady Kokish, Los Gatos, CA (US);
Yung-Ming Chen, Cupertino, CA (US);
Jason Van Sciver, Los Gatos, CA (US);
Roberto Listek, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 791 days.

(21) Appl. No.: 10/315,457

(22) Filed: Dec. 9, 2002

(51) Int. Cl.
*B05C 13/02* (2006.01)
*B05C 5/02* (2006.01)
*B05D 1/02* (2006.01)

(52) U.S. Cl. .................. 118/500; 118/503; 118/320

(58) Field of Classification Search .......... 118/500, 118/503, 320; 427/2.1, 2.24
See application file for complete search history.

(56) References Cited

U.S. PATENT DOCUMENTS

| | | | | |
|---|---|---|---|---|
| 4,616,593 A | * | 10/1986 | Kawamura et al. | 118/303 |
| 4,645,649 A | * | 2/1987 | Nagao | 422/186.3 |
| 4,733,665 A | | 3/1988 | Palmaz | 128/343 |
| 4,800,882 A | | 1/1989 | Gianturco | 128/343 |
| 4,886,062 A | | 12/1989 | Wiktor | 128/343 |
| 4,893,623 A | * | 1/1990 | Rosenbluth | 606/192 |
| 4,977,901 A | | 12/1990 | Ofstead | 128/772 |
| 5,112,457 A | | 5/1992 | Marchant | 204/165 |
| 5,298,276 A | * | 3/1994 | Jayaraman | 427/2.25 |
| 5,328,471 A | | 7/1994 | Slepian | 604/101 |
| 5,455,040 A | | 10/1995 | Marchant | 424/426 |
| 5,464,650 A | | 11/1995 | Berg et al. | 427/2.3 |
| 5,578,073 A | | 11/1996 | Haimovich et al. | 623/1 |
| 5,605,696 A | | 2/1997 | Eury et al. | 424/423 |
| 5,667,767 A | | 9/1997 | Greff et al. | 424/9.411 |
| 5,670,558 A | | 9/1997 | Onishi et al. | 523/112 |
| 5,700,286 A | | 12/1997 | Tartaglia et al. | 623/1 |
| 5,716,981 A | | 2/1998 | Hunter et al. | 514/449 |
| 5,824,049 A | | 10/1998 | Ragheb et al. | 623/1 |
| 5,830,178 A | | 11/1998 | Jones et al. | 604/49 |
| 5,837,313 A | | 11/1998 | Ding et al. | 427/2.21 |
| 5,851,508 A | | 12/1998 | Greff et al. | 424/9.411 |
| 5,858,746 A | | 1/1999 | Hubbell et al. | 435/177 |
| 5,865,814 A | | 2/1999 | Tuch | 604/265 |
| 5,873,904 A | | 2/1999 | Ragheb et al. | 623/1 |
| 5,971,954 A | | 10/1999 | Conway et al. | 604/96 |
| 5,980,928 A | | 11/1999 | Terry | 424/427 |
| 5,980,972 A | | 11/1999 | Ding | 427/2.24 |
| 6,015,541 A | | 1/2000 | Greff et al. | 424/1.25 |
| 6,042,875 A | | 3/2000 | Ding et al. | 427/2.24 |

(Continued)

FOREIGN PATENT DOCUMENTS

EP     0 665 023     8/1995

(Continued)

OTHER PUBLICATIONS

Fisher Scientific Catalogue, pp. 504-507 (1988).*

*Primary Examiner*—Laura Edwards
(74) *Attorney, Agent, or Firm*—Squire, Sanders & Dempsey L.L.P.

(57) ABSTRACT

A coating and drying apparatus for the application of a coating substance to a stent and drying the stent is provided.

12 Claims, 5 Drawing Sheets

U.S. PATENT DOCUMENTS

| | | | |
|---|---|---|---|
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,562,136 B1 * | 5/2003 | Chappa et al. | 118/500 |

FOREIGN PATENT DOCUMENTS

| | | |
|---|---|---|
| EP | 0 970 711 | 1/2000 |
| WO | WO 00/12147 | 3/2000 |
| WO | WO 00/64506 | 11/2000 |
| WO | WO 01/01890 | 1/2001 |

* cited by examiner

APPARATUS AND METHOD FOR COATING AND DRYING MULTIPLE STENTS

TECHNICAL FIELD

This invention relates to an apparatus used in the process of coating and drying stents, and more particularly provides an apparatus for coating and drying a plurality of stents.

BACKGROUND

Blood vessel occlusions are commonly treated by mechanically enhancing blood flow in the affected vessels, such as by employing a stent. Stents act as scaffolding, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer. In order to quicken the process, the stents may be baked so that the solvent evaporates quickly.

Shortcomings of the above-described method of medicating a stent is the potential for shot to shot variation of the coating weight and the need for baking or otherwise drying each stent after the coating application. These two shortcomings limit production throughput. Specifically, after each coating process (e.g., primer, drug coat, topcoat), the stent must be weighed to calculate the amount of drug and polymer deposited onto the stent. In addition, up to two hours bake time can be required to evaporate the solvent from the stent.

Accordingly, a new apparatus for spraying coating is needed to increase production throughput.

SUMMARY

In accordance with one embodiment, a stent coating and drying apparatus is provided, comprising a chamber for receiving a cartridge, the chamber including a drying section and a spray coating section. The cartridge can have a plurality of stent mandrels for supporting the stents. The cartridge is capable of moving a stent supported on a stent mandrel from the spray coating section to the drying section or from the drying section to the spray coating section of the chamber. A spray applicator is used for spraying the coating substance onto the stent when the stent is positioned in the spray coating section of the chamber. In one embodiment, the chamber is in communication with a heated gas supply for supplying heated gas to the drying section of the chamber. The stent mandrels can be evenly distributed and extending out from the circumference of the cartridge. The spray coating section is at least partially sectioned off from the drying section of the chamber. Additionally, the drying section can include a vent that discharges the heated gas that is applied into the chamber.

In accordance with another embodiment, a cartridge is provided, comprising a core and a plurality of stent mandrels extending outwards from a circumference of the core, each stent mandrel capable of supporting a stent. A first clutch can be coupled to the core and capable of being removably coupled to a first shaft such that rotation of the first shaft enables rotation of the core. A second clutch can be coupled to the plurality of stent mandrels and capable of being removably coupled to a second shaft such that rotation of the second shaft enables rotation of the stent mandrels.

In accordance with another embodiment, a system for forming a coating on a stent is provided comprising a hub for holding at least one cartridge, the cartridge capable of having a plurality of stents supported thereon; a chamber capable of receiving the cartridge for the application of a coating substance to the stents; an arm capable of moving the cartridge between the hub and the chamber; and a spray applicator capable of applying a coating composition to the stent.

In accordance with another embodiment, a method for forming a coating on a stent is provided, comprising: placing a cartridge within a chamber, the chamber including a drying section and a spray coating section, the cartridge having a plurality of stent mandrels each supporting a stent; positioning a stent in the spray coating section of the chamber; and applying a coating composition to the stent in the spray coating section of the chamber.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
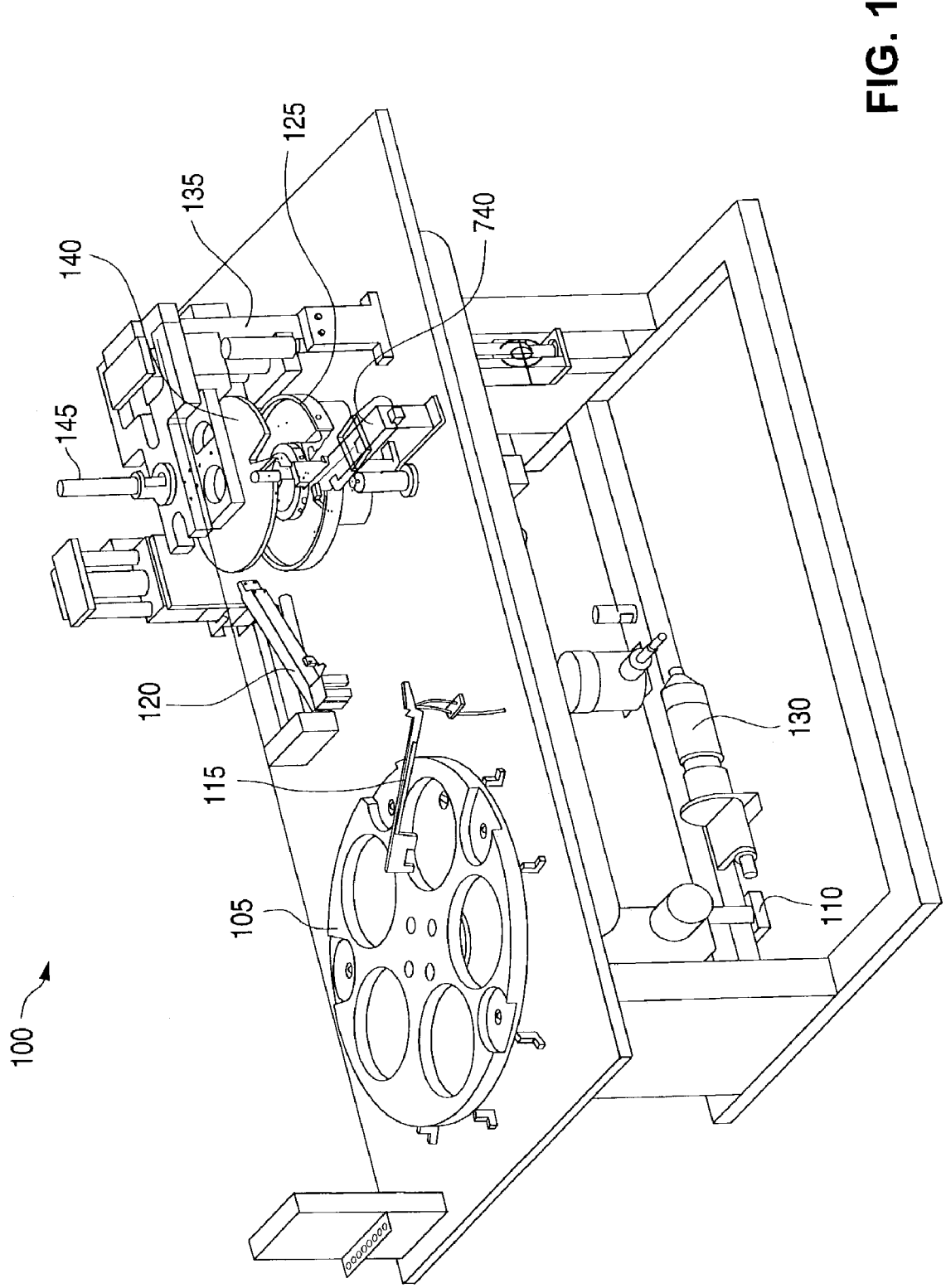
FIG. 1 is a diagram illustrating a multiple stent coater/dryer apparatus.

FIG. 1 is a diagram illustrating a multiple stent coater/dryer apparatus 100. The multiple stent coater/dryer apparatus 100 enables the coating and simultaneous drying of stents, thereby increasing throughput. Bare stents are manually loaded onto a circular cartridge 500 (FIG. 5), which can hold twelve to eighteen stents in one embodiment of the invention. The cartridge 500 is then manually placed in a loading bay on a circular-shaped hub 105. An engine 110 rotates the hub 105 in a counter clockwise direction such that a handle 510 of the cartridge 500 passes through a gate 115, thereby indicating that the cartridge 500 is oriented correctly so that an arm 120 can pick up the cartridge 500.

Figure 6:
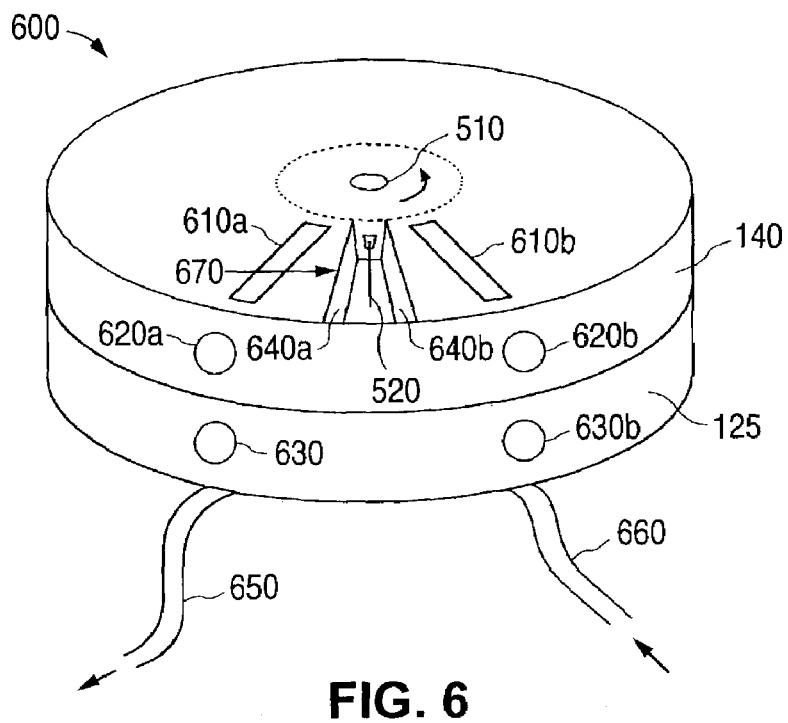
FIG. 6 is a diagram illustrating the coating/drying chamber holding a cartridge.

After the cartridge 500 passes through the gate 115, the arm 120 picks up the cartridge 500 via the handle 510 and carries the cartridge 500 to a secondary chamber for coating and drying stents on the cartridge 500. The arm 120 then securely places the cartridge 500 into a base 125 of a coating/drying chamber 600 (FIG. 6). After placement, a lever 135 lowers a cap 140 onto the base 125 so as to form the coating/drying chamber 600. The lever 135 also lowers an anvil 145 onto the handle 510 of the cartridge 500. As will be discussed further below, the cartridge 500 rotates within the coating/drying chamber 600 such that while one stent is being coated by a coating applicator 740, other stents mounted on the cartridge 500 are dried (and/or preheated for coating). In an embodiment of the invention, a dryer 130 is in communication with the coating/drying chamber 600 to supply heated air to dry the stents mounted on the cartridge 500.

Figure 2:
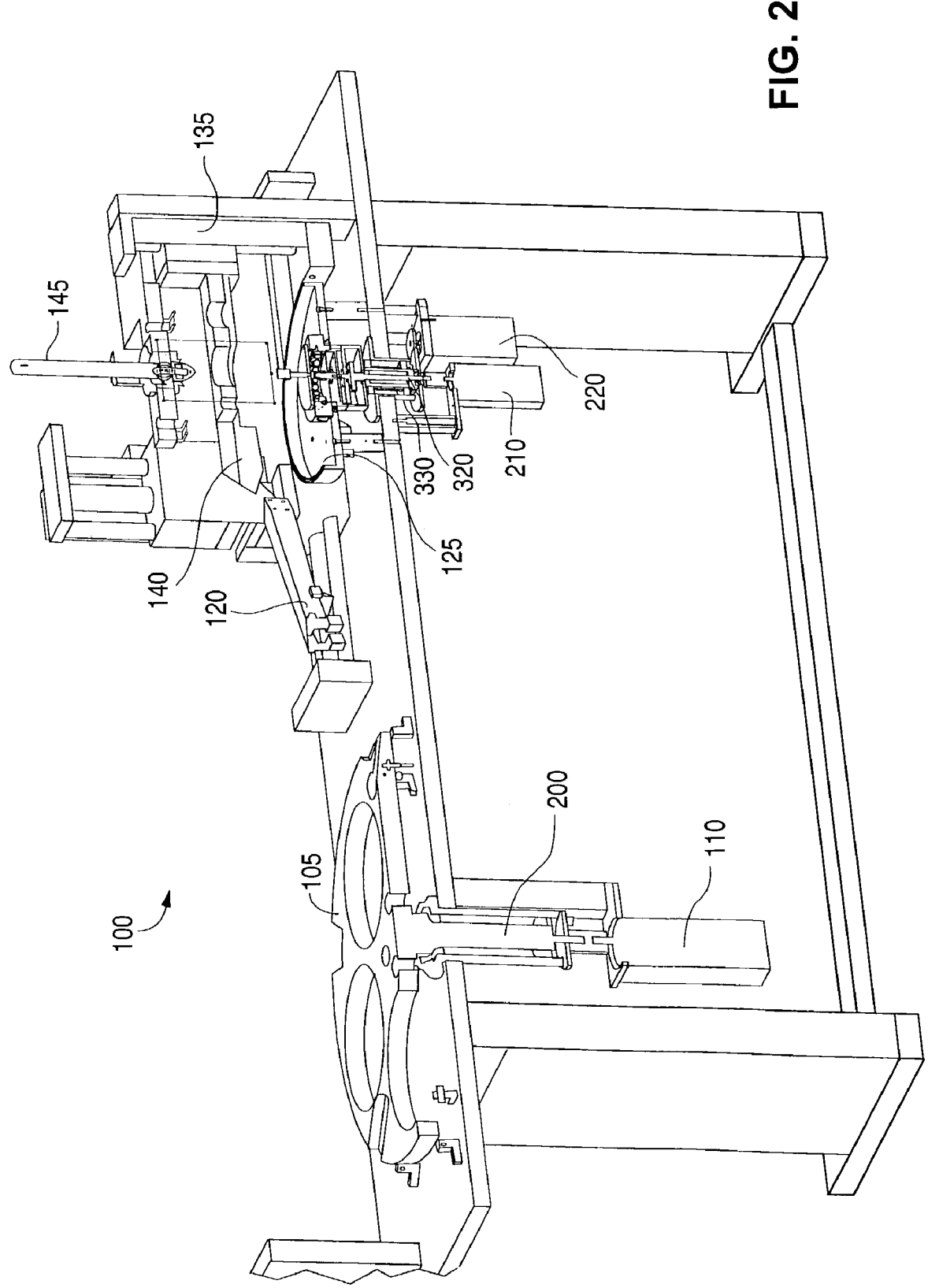
FIG. 2 is a diagram illustrating a cross section of the multiple stent coater/dryer apparatus.

FIG. 2 is a diagram illustrating a cross section of the multiple stent coater/dryer apparatus 100. The apparatus includes a shaft 200 coupled to the engine 110 and the hub 105 that is used to rotate the hub 105. Engines 210 and 220 rotate an inner shaft 320 and an outer shaft 330, respectively. As will be discussed further below, the outer shaft 330 rotates the cartridge 500 and the inner shaft 320 rotates stent mandrels 520 (FIG. 5) of the cartridge 500.

Figure 3:
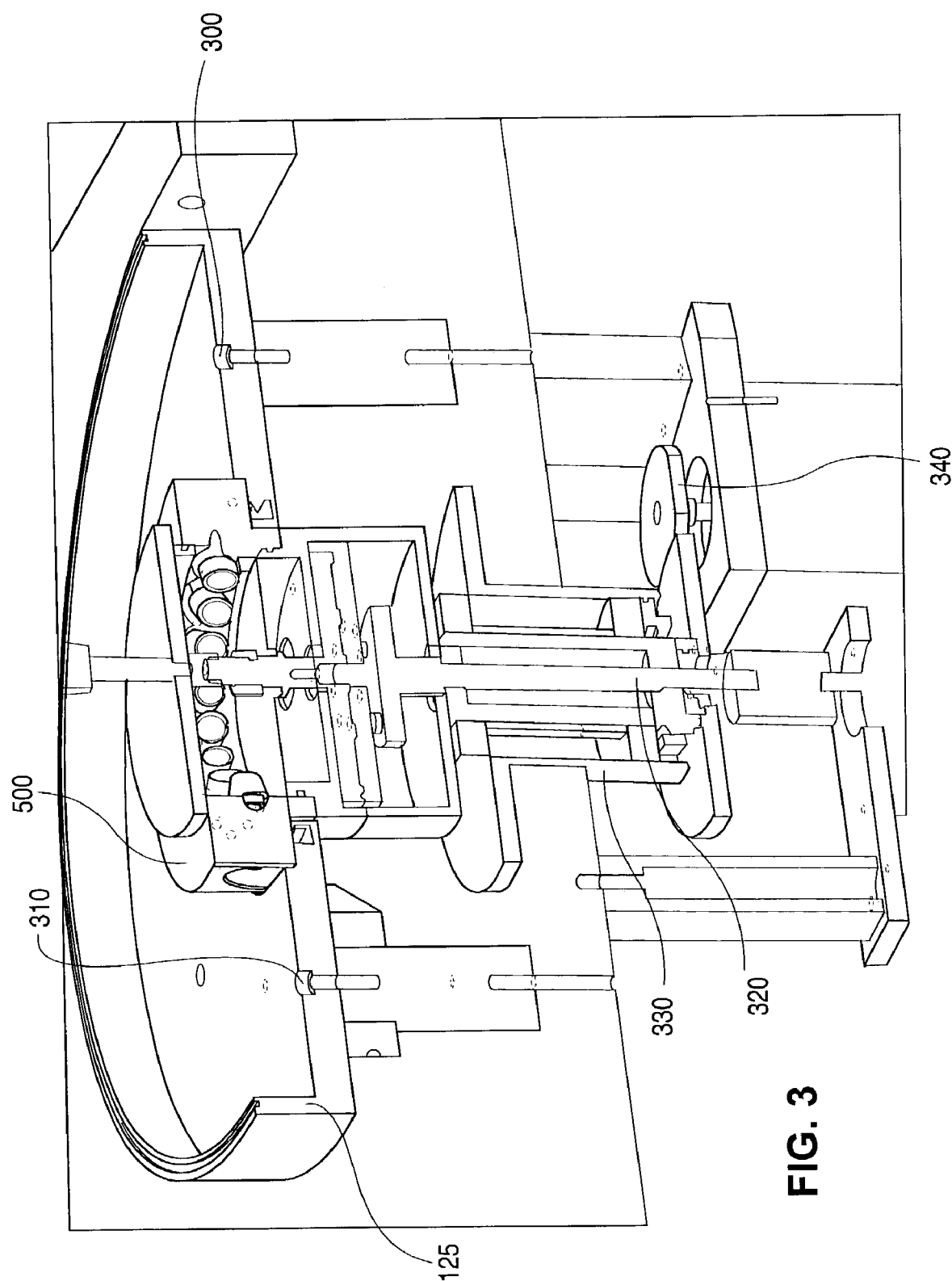
FIG. 3 is a diagram illustrating a cross section of a portion the coating/drying chamber.

FIG. 3 is a diagram illustrating a cross section of a portion the coating/drying chamber 600. The chamber 600 includes the base 125 and the cap 140. The base 125 includes an air inlet 300 for receiving heated air and an air outlet 310 for exhausting heated air, thereby enabling the circulation of heated air within the chamber 600. The outer shaft 330 is coupled to the cartridge 500 via an outer clutch 550 (FIG. 5) and the components engage by the pressure applied by the anvil 145. Accordingly, lifting of the lever 135 will enable the decoupling of the cartridge 500 from the outer shaft 330. Coupled to the outer shaft 330 is gear 340, which is interlocked with the outer shaft 330 such that rotation of the gear 340 causes outer shaft 330 to rotate. The inner shaft 320 is also coupled to the cartridge 500 via an inner clutch 540 (FIG. 5) via pressure applied by the anvil 145. Rotation of the inner shaft 320 causes the mandrels 520 to rotate during spraying and drying, as will be discussed further below.

Figure 4:
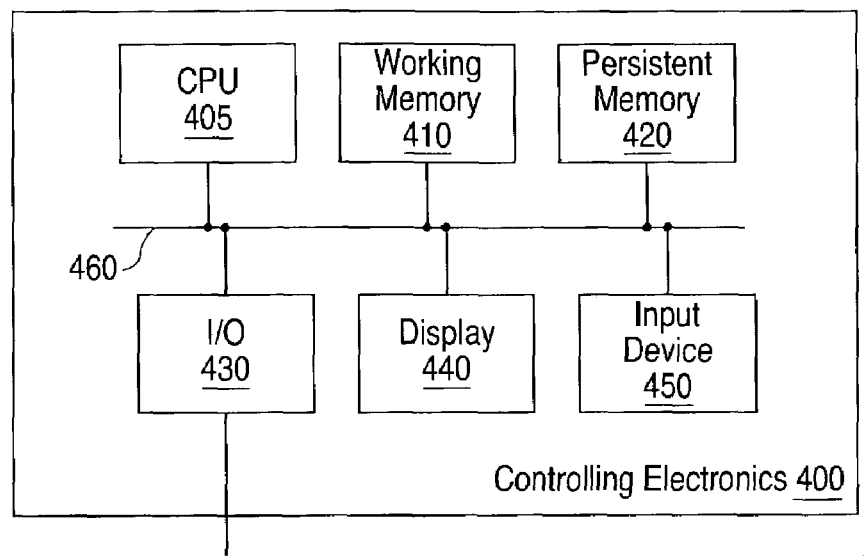
FIG. 4 is a block diagram illustrating controlling electronics in accordance with one embodiment of the present invention.

FIG. 4 is a block diagram illustrating controlling electronics 400 in accordance with an embodiment of the present invention. In an embodiment of the invention, the controlling electronics 400 controls substantially all aspects of the multiple stent coater/dryer apparatus 100. Specifically, the controlling electronics 400 controls rotation of the hub 105; linear movement of the arm 120; vertical movement of the lever 135; temperature and pressure of air produced by the dryer 130; rotation of the outer shaft 330; rotation of the inner shaft 320; and the coating applicator 740.

The controlling electronics 400 includes a central processing unit (CPU) 405; working memory 410; persistent memory 420; input/output (I/O) interface 430; display 440 and input device 450, all communicatively coupled to each other via system bus 460. CPU 405 may include an Intel Pentium® microprocessor, a Motorola PowerPC® microprocessor, or any other processor capable to execute software to control the multiple stent coater/dryer apparatus 100 that is stored in persistent memory 420. Working memory 410 may include random access memory (RAM) or any other type of read/write memory devices or combination of memory devices. Persistent memory 420 may include a hard drive, read only memory (ROM) or any other type of memory device or combination of memory devices that can retain data after controlling electronics 400 is shut off. I/O interface 430 is communicatively coupled, via wired or wireless techniques, to the components of the multiple stent coater/dryer apparatus 100 that the controlling electronics 400 controls. Display 440 may include a liquid crystal display or other display device. Input device 450 may include a keyboard, mouse, or other device for inputting data, or a combination of devices for inputting data.

One skilled in the art will recognize that the controlling electronics 400 may also include additional devices, such as network connections, additional memory, additional processors, LANs, input/output lines for transferring information across a hardware channel, the Internet or an intranet, etc. One skilled in the art will also recognize that the programs and data may be received by and stored in the system in alternative ways.

Figure 5:
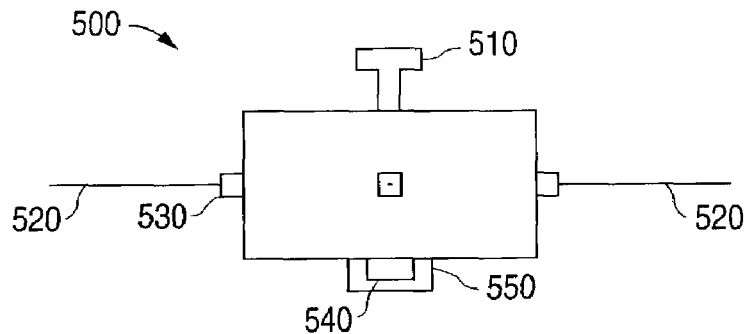
FIG. 5 is a diagram illustrating a profile of the cartridge.

FIG. 5 illustrates a profile of the cartridge 500. The cartridge includes a plurality of stent mandrels 520 and associated knobs 530, the handle 510, the inner clutch 540, and the outer clutch 550. The arm 120 picks up the cartridge 500 via the handle 510 and moves it between the hub 105 and the base 125. Specifically, before coating and drying, the arm 120 moves the cartridge 500 via the handle 510 from the hub 105 to the base 125. After coating and drying, the arm 120 removes the cartridge 500 from the base 125 and returns it to the hub 105. The stent mandrels 520 hold stents during coating and drying processes. In an embodiment, the stent mandrels 520 includes up to eighteen stent mandrels 520 distributed around the periphery of the cartridge 500. The inner clutch 540 is coupled to the stent mandrels 520 such that rotation of the inner clutch 540 causes rotation of the stent mandrels 520. This allows rotation of the stents along the longitudinal axis of the stents. Rotational forces applied to the outer clutch 550 causes rotation of the entire cartridge 500.

FIG. 6 is a diagram illustrating the coating/drying chamber 600 holding the cartridge 500. The drying chamber 600 comprises the base 125 and the cap 140 and holds the cartridge 500, which rotates counter clockwise within the drying chamber 600 in an embodiment. The base 125 and cap 140 both have open cylinder shapes that when combined form a closed cylindrical shape.

Figure 7:
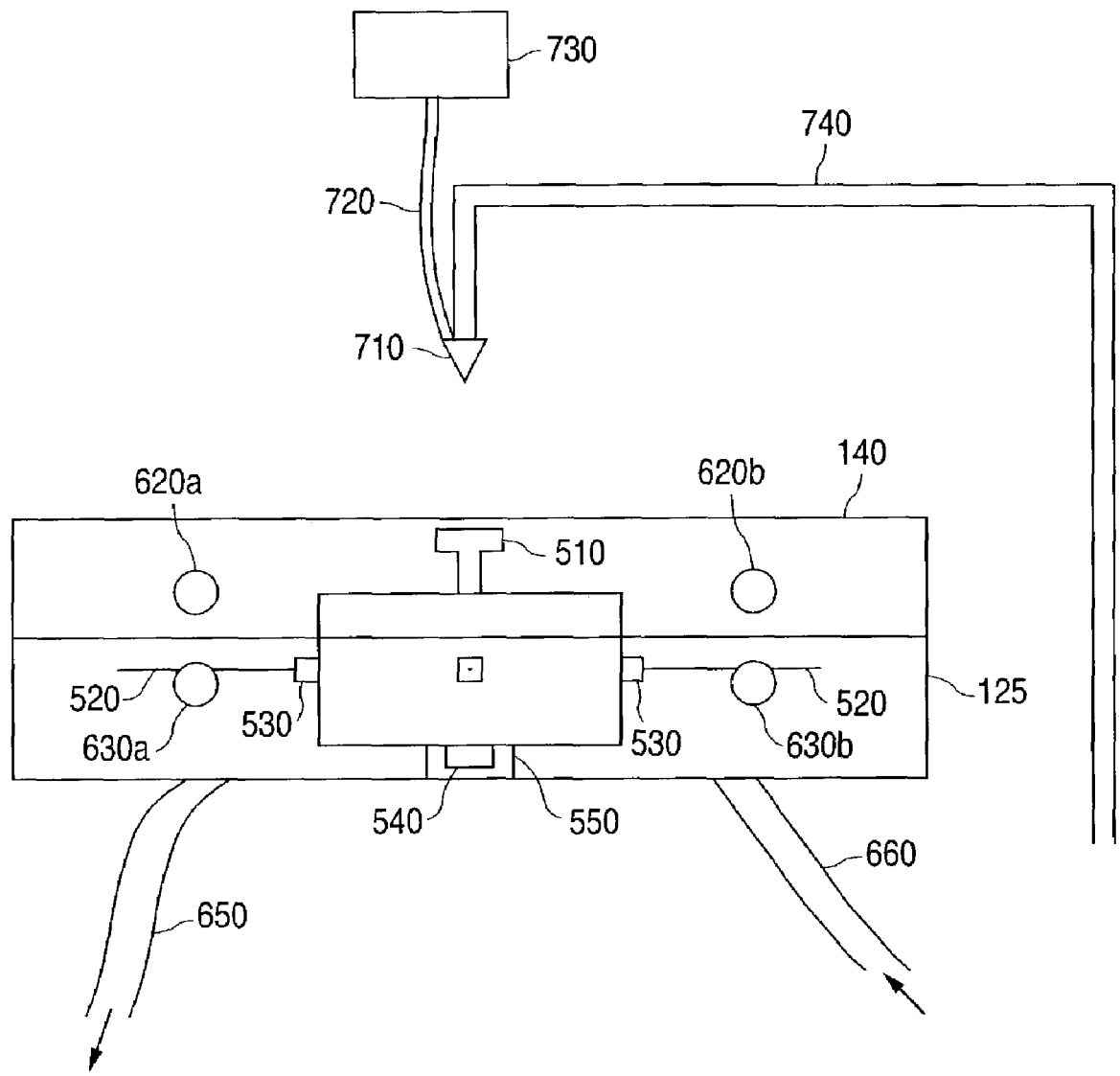
FIG. 7 is a diagram illustrating the coating/drying chamber holding a cartridge with a coating applicator.

The coating/drying chamber 600 also includes a spray chamber 670, which exposes a single stent mandrel 520 to spray coating from the coating applicator 740 (FIG. 7). The spray chamber 670 is formed by an open section of the cap 140 with gates 640a and 640b (also referred to as flaps) sectioning off the remainder of the spray chamber 670 from the coating/drying chamber 600. The gates 640a and 640b are coupled to the top of cap 140 with hinges such that pressure applied to the gates 640a and 640b (e.g., via knobs 530) cause them to rotate upwards from a vertical position to a horizontal position thereby enabling the stent mandrels 520 to pass through the gates 640a and 640b.

The remainder of the coating/drying chamber 600 forms a drying chamber within which circulates heated air to preheat stents before coating and to dry stents after coating. A tubing 660 couples dryer 130 to the drying chamber section of the coating/drying chamber 600 via inlet 300 for receiving heated air. The heated air rotates through the coating/drying chamber 600 in a counter clockwise direction and exits via outlet 310, which is coupled to a tubing 650. The tubing 650 can be coupled to a filtering device (not shown) or other device for collecting and/or filtering the heated air, which may contain chemicals (e.g., solvents and drugs) from the coating process.

During rotation of the cartridge 500 within the coating/drying chamber 600, the knobs 530, which are metallic, push open the gate 640a so that the a stent mandrel 520 can enter the spray chamber 670. In addition, the knobs 530 push open gate 640b so that a recently coated stent on a stent mandrel 520 can enter the drying chamber. A sensor (not shown) comprising a metal detector or other device detects and determines the position of at least one of the knobs 530 and provides feedback to control electronics 400, which then controls rotation of the cartridge 500 such that a stent mandrel 520 is positioned correctly in the spray chamber 670.

Adjacent to the spray chamber 670 are circular vents 620a and 620b located in the rim of the cap 140. Additionally, rectangular vents 610a and 610b are located on the top of the cap 140 adjacent to the spray chamber 670. The base 125 also includes two circular vents 630a and 630b located beneath vents 620a and 620b respectively. These vents enable excess heated air to vent from the drying section of the coating/drying chamber 600 without interfering with a coating process.

The coating process, as will be described in further detail in conjunction with FIG. 7, sprays a coating substance onto stents mounted on the stent mandrels 520. The coating substance can include a solvent and a polymer dissolved in the solvent and optionally a therapeutic substance or a drug added thereto. Representative examples of polymers that can be used to coat a stent include ethylene vinyl alcohol copolymer (commonly known by the generic name EVOH or by the trade name EVAL), poly(hydroxyvalerate); poly (L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

FIG. 7 is a diagram illustrating the coating/drying chamber 600 holding the cartridge 500 with the coating applicator 740 positioned adjacent thereto. The coating applicator 740 includes a nozzle 710, reservoir 730 and tubing 720 that places the nozzle 710 in fluid communication with the reservoir 730. The coating applicator 740 is communicatively coupled to controlling electronics 400, which controls movement of the coating applicator 740 as well as dispensation of a coating substance, stored in the reservoir 730, via nozzle 710 onto a stent in the spray chamber 670. During a spray coating process, the coating applicator 740 can move back and forth along the length of the stent to spray the stent. In addition, the stent mandrel 520 holding the stent also rotates during the spray coating process to ensure that the stent is equally coated with the coating substance.

After spraying, the controlling electronics 400 causes the cartridge 500 to rotate in a counter clockwise direction such that one of the knobs 530 pushes open gate 640b so that the coated stent can enter the drying portion of coating/drying chamber 600. The cartridge 500 can make a full 360-degree revolution so that the stent can go through a subsequent spray coating process, thereby enabling multiple layers of a coating substance or multiple layers of a plurality of different coating substances to be formed on a stent.

In an embodiment of the invention, the coating/drying chamber 600 includes a plurality of spray chambers 670 and coating applicators 740 so that a plurality of different coating substances can be dispensed onto a stent during a coating/drying cycle.

In an example coating/drying process, the dryer 130 supplies heated air having a temperature of, for example, 50 to 80 degrees celsius. The heated air can circulate within the drying section of the coating/drying chamber 600 at a speed of up to about 20 meters/second. The cartridge 500 makes 20 to 60 revolutions per process, leading to 20 to 60 coating layers applied to each stent mounted on the stent mandrels 520. The coating applicator can spray a stent mounted on the stent mandrel 520 for about five to ten seconds at a rate of about 50 cubic millimeters per minute. The nozzle 710 can use about 15 psi atomization air pressure to atomize the composition dispensed from the nozzle 710.

Accordingly, the multiple stent coater/dryer apparatus 100 enables elimination of a long final oven bake of the stents because the solvent is removed after application of each thin layer. Further, the multiple stent coater/dryer apparatus 100 minimizes drug-solvent interaction because the solvent is removed from each layer immediately after the composition is applied. In addition, the multiple stent coater/dryer apparatus 100 enables minimization of extraction of the drug in a lower layer into an upper layer because the solvent is removed immediately for each layer after coating. Another benefit is that the multiple stent coater/dryer apparatus 100 enables minimal handling between applications of layers. For example, the stents do not need to be weighed between applications of layers. An additional benefit is that the multiple stent coater/dryer apparatus 100 enables deposition of a higher coating weight per layer/coating cycle by drying off substantially all of the solvent after each spray coating cycle. Finally, the multiple stent coater/dryer apparatus 100 enables preheating of each stent prior to each cycle for better wetting.

The foregoing description of the illustrated embodiments of the present invention is by way of example only, and other variations and modifications of the above-described embodiments and methods are possible in light of the foregoing teaching. Components of this invention may be implemented using a programmed general purpose digital computer, using application specific integrated circuits, or using a network of interconnected conventional components and circuits. Connections may be wired, wireless, modem, etc. The embodiments described herein are not intended to be exhaustive or limiting. The present invention is limited only by the following claims.

What is claimed is:

1. A stent coating and drying apparatus, comprising:
   a chamber including a drying section, a spray coating section and a gate separating the drying section and the spray coating section; and
   a cartridge disposed in the chamber, the cartridge having a plurality of stent mandrels for supporting stents, wherein the cartridge is capable of moving a stent supported on a stent mandrel from the spray coating section to the drying section or from the drying section to the spray coating section of the chamber, and wherein the gate opens to allow the stent to move from the spray coating section to the drying section or from the drying section to the spray coating section and closes after the stent movement.

2. The apparatus of claim 1, additionally including a spray applicator for spraying the coating substance onto the stent when positioned in the spray coating section of the chamber.

3. The apparatus of claim 1, wherein the chamber is in communication with a heated gas supply for supplying heated gas to the drying section of the chamber.

4. The apparatus of claim 1, wherein the stent mandrels are evenly distributed and extending out from a circumference of the cartridge.

5. The apparatus of claim 1, wherein the spray coating section is at least partially sectioned off from the drying section.

6. The apparatus of claim 1, wherein the drying section includes a vent that discharges a gas that is applied into the chamber.

7. The apparatus of claim 1, wherein the cartridge is capable of rotating the stent mandrels about the longitudinal axis of the stent.

8. The apparatus of claim 1, wherein the chamber includes an upper portion capable of mating with a lower portion subsequent to the placement of the cartridge in the chamber.

9. The apparatus of claim 1, further including a sensor capable of determining if a stent mandrel is correctly positioned in the spray coating section.

10. The apparatus of claim 1, additionally including a spray applicator capable of spraying the coating substance onto the stent, wherein the spray applicator is capable of moving back and forth along the length of the stent.

11. The apparatus of claim 1, wherein each of the stent mandrels extends out from a knob positioned about a circumference of the cartridge.

12. A stent coating and drying apparatus comprising:
   a chamber including a drying section and a spray coating section; and
   a cartridge disposed in the chamber, the cartridge having a plurality of stent mandrels for supporting stents, wherein the cartridge is capable of moving a stent supported on a stent mandrel from the spray coating section to the drying section or from the drying section to the spray coating section of the chamber, wherein the chamber includes gates for separating the spray coating section from the drying section and wherein knobs are positioned about a circumference of the cartridge, the knobs capable of pushing the gates open to rotate a stent from the spray coating section to the drying section and a stent from the drying section to the spray coating section.

* * * * *